US011253682B1

(12) United States Patent
 Qu et al.

(10) Patent No.: US 11,253,682 B1
(45) Date of Patent: Feb. 22, 2022

(54) DIVIDED TIP URINARY CATHETER WITH BALLOON INFLATION GENERATED METHOD OF URINE DRAINAGE

(71) Applicants: Shaolong Qu, Chaska, MN (US); Youshi Mi, Chaska, MN (US); Weihao Qu, Chaska, MN (US)

(72) Inventors: Shaolong Qu, Chaska, MN (US); Youshi Mi, Chaska, MN (US); Weihao Qu, Chaska, MN (US)

(*) Notice: Subject to any disclaimer, the term of this patent is extended or adjusted under 35 U.S.C. 154(b) by 0 days.

(21) Appl. No.: 17/350,913

(22) Filed: Jun. 17, 2021

(51) Int. Cl.
 *A61M 25/10* (2013.01)

(52) U.S. Cl.
 CPC . *A61M 25/1011* (2013.01); *A61M 2202/0496* (2013.01); *A61M 2210/1085* (2013.01)

(58) Field of Classification Search
 CPC ...... A61M 25/1011; A61M 2202/0496; A61M 2210/1085; A61M 2025/0034; A61M 2025/0037; A61M 25/0668; A61M 25/0029; A61M 25/007; A61M 2025/0079
 See application file for complete search history.

(56) References Cited

U.S. PATENT DOCUMENTS

| | | | | |
|---|---|---|---|---|
| 5,403,280 | A * | 4/1995 | Wang | A61M 25/1011 604/103.06 |
| 5,441,485 | A * | 8/1995 | Peters | A61M 25/1002 604/101.01 |
| 5,549,555 | A * | 8/1996 | Sohn | A61M 25/1002 604/101.01 |
| 6,086,557 | A * | 7/2000 | Morejohn | A61M 1/3659 604/101.01 |
| 2002/0120233 | A1 * | 8/2002 | Eidenschink | A61M 25/104 604/96.01 |
| 2002/0177869 | A1 * | 11/2002 | Eidenschink | A61M 25/09041 606/194 |
| 2004/0167463 | A1 * | 8/2004 | Zawacki | A61M 25/0026 604/43 |
| 2007/0287967 | A1 * | 12/2007 | Hekmat | A61M 25/008 604/284 |
| 2009/0306757 | A1 * | 12/2009 | Meyer | A61M 25/0105 623/1.11 |
| 2014/0214002 | A1 * | 7/2014 | Lieber | A61M 25/1011 604/509 |
| 2017/0157370 | A1 * | 6/2017 | Agah | A61M 25/0097 |
| 2017/0252504 | A1 * | 9/2017 | Tal | A61M 25/003 |
| 2018/0229010 | A1 * | 8/2018 | Walzman | A61M 25/0029 |
| 2019/0224455 | A1 * | 7/2019 | Hakky | A61M 25/0074 |
| 2020/0368492 | A1 * | 11/2020 | Nasser | A61M 25/0074 |

* cited by examiner

*Primary Examiner* — Adam Marcetich
(74) *Attorney, Agent, or Firm* — Johnson & Phung LLC; Thomas N. Phung

(57) ABSTRACT

The present invention discloses a urinary catheter that utilizes balloons to generate a method of urine drainage. The disclosed invention does not implement a traditional drainage port and avoids an exposed catheter tip. Rather, this invention consists of a multi-lumen shaft with a divided tip that generates a horizontal aperture for urine drainage when separated. The invention utilizes retention members that can take the form of multiple expandable balloons or a singular, expandable, central balloon. The balloon element can consists of balloons that are attached separately to each divided tip or one balloon shared with adjacent divided tips so that when the balloon element expands, a communication channel is revealed between the bladder and the central lumen of the shaft, ultimately generating a method of urine drainage.

11 Claims, 9 Drawing Sheets

DIVIDED TIP URINARY CATHETER WITH BALLOON INFLATION GENERATED METHOD OF URINE DRAINAGE

CROSS REFERENCE TO RELATED APPLICATIONS

Not Applicable

STATEMENT OF FEDERALLY SPONSORED RESEARCH OR DEVELOPMENT

Not Applicable

REFERENCE CITED

U.S. Pat. No. 10,195,394 B2 February 2019 Havard
U.S. Pat. No. 8,636,724 B2 January 2014 Wiita et al.
2006/0167406 A1 July 2006 Quinn
U.S. Pat. No. 3,954,110 May 1976 Hutchison
U.S. Pat. No. 3,811,448 May 1974 Morton
U.S. Pat. No. 3,889,686 June 1975 Duturbure
U.S. Pat. No. 5,250,029 October 1993 Lin et al.
2008/0071250 A1 March 2008 Crisp
2010/0234668 A1 September 2010 Roeder
2009/0221992 A1 September 2009 Hannon et al
2011/0190737 A1 August 2011 Rocco
2013/0281926 A1 October 2013 Raux et al
2012/0203210 A1 August 2012 Schanz et al
2015/0359996 A1 December 2015 Arora et al
U.S. Pat. No. 3,421,509 January 1969 Fiore
U.S. Pat. No. 3,438,375 March 1969 Ericson
U.S. Pat. No. 4,022,216 May 1977 Stevens
U.S. Pat. No. 4,154,242 May 1979 Termanini
U.S. Pat. No. 4,217,903 August 1980 Witherow
U.S. Pat. No. 4,701,162 October 1987 Rosenberg
U.S. Pat. No. 4,233,983 November 1980 Rocco
U.S. Pat. No. 4,781,677 November 1988 Wilcox
U.S. Pat. No. 4,820,270 April 1989 Hardcastle, et al
U.S. Pat. No. 4,973,301 November 1990 Nissenkorn
U.S. Pat. No. 5,096,454 March 1992 samples
2009/0030370 A1 January 2009 Nishtala; Vasu; et al.
2011/0082444 A1 April 2011 Mayback; Gregory L.; et al.
2008/0125757 A1 May 2008 Gobel; Fred
2002/0107540 A1 August 2002 Whalen et al.
2005/0228402 A1 October 2005 Hofmann
2008/0103443 A1 May 2008 Kabrick et al.
2005/0186370 A1 August 2005 Hamilton et al.

BACKGROUND OF THE INVENTION a. Field of the Invention

This invention relates to catheters designed to be inserted into bodily cavities. Specifically, this invention relies on divided tips that generate a method of fluid drainage when separated by expandable balloons that also serve as retention elements.

b. Background of the Prior Art

Catheters are utilized in different parts of the human body to deliver or withdraw fluids to and from body vessels, ducts and cavities. For a better description of the invention, urinary catheters are discussed here. Urinary catheters allow for the passive drainage of urine when they are advanced into the bladder through the urethra. However, the same feature can be applied to catheters when used in different body areas.

Urinary catheters are often utilized when individuals experience difficulty eliminating urine from the bladder through native processes. Urinary catheters can also be used to empty the bladder before or following surgical procedures and may enable urine collection for testing even in instances of incontinence. The Foley catheter, the most commonly used indwelling urinary catheter, has been used in medical treatment for decades. It is commonly made of natural latex or silicone and consists of a valve lumen situated in parallel alongside a central drainage lumen. The central drainage lumen allows urine to travel from a drainage port within the bladder to a collection bag while the valve lumen connects an external valve to a balloon that serves as the retention element, securing the catheter tube within the bladder when inflated with a fluid such as sterile water.

While widely used, current commercially available indwelling catheters share underlying design flaws that frequently cause physical trauma to the bladder and catheter associated urinary tract infection (CAUTI). In many catheter designs, the catheter tip often protrudes into the bladder wall, damaging the urothelial lining of the bladder and impeding the bladder's antibacterial barrier. Additionally, the inward force produced by the flow of urine often causes the bladder wall to be suctioned onto the drainage port, also damaging the bladder wall and impeding urine drainage. These design flaws lead to increased risk of infection and irritation of the local tissue. In addition, because the drainage port is located above the inflated retention balloon, urine below the drainage port fails to drain from the bladder. The residual urine is prone to infection with bacterial capable of producing urease, an enzyme that hydrolyzes urea and leads to a rise in pH of the urine. Subsequently, this leads to the deposition and aggregation of crystalline material in the bladder, forming encrustations that can eventually block the flow of the urine through the catheter. Ultimately, frequent infections as a result of catheter usage may cause discomfort. Untreated infections may result in serious illnesses or prove fatal for certain patients. Therefore, an alternative design to current catheter designs is in great need. The described invention provides a manufacturable solution that addresses previously mentioned design related issues associated with concurrently used catheter.

U.S. Pat. No. 8,636,724 B2 and U.S. Pat. No. 4,022,216 both disclose a catheter design that utilizes a two-balloon system where a drainage port can be found in between a balloon that encapsulates the catheter tip and the retention element balloon. While an encapsulated tip reduces catheter induced damage to the bladder's lining, residual urine due to an elevated drainage port remains an issue.

U.S. Pat. No. 9,126,008 B2 discloses a urinary catheter design with at least one drainage port positioned in between two balloons on the distal end of the catheter. While this design mitigates issues of residual urine by avoiding an elevated drainage port, the vertical nature of the drainage port may prevent the flow of urine when the drainage ports sink into the urethra due to the body's posture or movement.

U.S. Pat. No. 10,195,394 B2 introduces a urinary catheter design with an inflatable balloon retention element attached to the catheter tip and a vertical drainage port situated just below. Again, in order to attenuate issues of residual urine, the lowered position and vertical nature of the drainage port maintain complications involving the blockage of the drainage port when it sinks into the urethra.

U.S. Pat. No. 4,575,371 discloses a urinary catheter with retention balloons arranged below the drainage port opening in order to prevent contact between the catheter tip and the bladder wall. This design leads to the elevation of the drainage port due to the lower placement of balloons, maintaining the issue of residual urine when urine levels fall below the drainage port.

BRIEF SUMMARY OF THE INVENTION

This invention offers solutions to previously mentioned challenges that accompany urinary catheter usage through the implementation of a divided catheter tip that uses balloon inflation to separate and reveal a urine drainage opening with a horizontal aperture that is perpendicular to the flow of urine down the central lumen. By avoiding exposed catheter tips and traditional drainage ports that are elevated or have vertical cross sections, this design prevents local tissue damage by the catheter tip, the inward suctioning of the bladder walls toward the drainage port, residual urine due to drainage port elevation, and risk of the drainage port sinking into the urethra due to bodily posture or movement.

Unless otherwise indicated, "distal" and "proximal" refers to relative positions toward the catheter tip that is inserted into the urethra and the base of the catheter connected to a collection bag, respectively. The term "inlet" and "drainage port" all refer to the passageway of urine in the prior art design.

The catheter consists of a flexible shaft with multiple lumens. The central lumen allows for bodily fluid like urine to travel from bodily cavities to an external collection bag. Other lumens, configured approximately equidistant from the central lumen, deliver sterile water to connected balloon elements, allowing for balloon inflation.

The distal end of the catheter is divided into separate tips of at least two, with each tip connected to its own balloon element or a balloon element shared with adjacent tips. When a singular balloon element is utilized, its expansion separates the tips of the catheter's distal end, revealing a horizontal aperture at the distal end of the central lumen, allowing for urine drainage. When multiple balloon elements are utilized, expansion of the balloon elements against each other will reveal a horizontal aperture at the distal end of the central lumen.

The balloon elements also function as retention elements, securing the catheter in the bladder, as well as protective elements that prevent the catheters tips from touching the bladder wall.

The distal end of the central lumen will be exposed as horizontal aperture situated at the junction between the bladder and the urethra. No additional drainage ports or inlets are presented in this invention.

BRIEF DESCRIPTION OF THE SEVERAL VIEWS OF THE DRAWING

The drawings referred in the present invention as below.

DETAILED DESCRIPTION OF THE INVENTION

Figure 1:
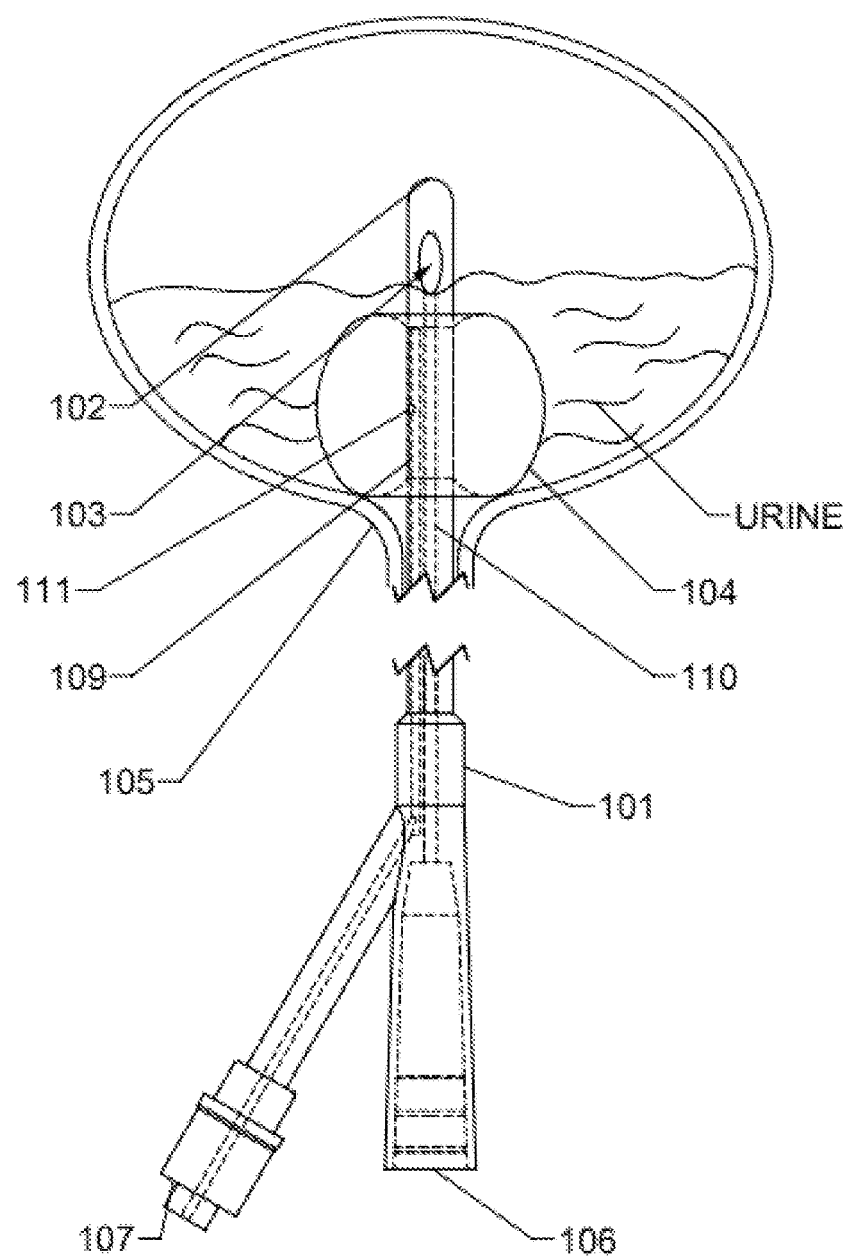
FIG. 1 illustrates the commercially available Foley Catheter in-situ.

FIG. 1 depicts the prior art design of commercially available Foley catheter where inflated balloon 104 is used to retain the distal end of catheter 101 within bladder 105. Valve 107 is used to inject sterile water to inflate balloon 104 through valve lumen 109 and inflation pot 111. Urine travels from drainage port 103 through central lumen 110 towards funnel 106, ultimately draining into an external collection bag.

The position of catheter tip 102 above retention balloon 104 exposes the catheter tip within bladder, allowing the catheter tip to make frequent contact with the bladder wall, leading to discomfort, damage of the bladders mucosal lining, and increased risk for urinary tract infection.

Similar to catheter tip 102, drainage port 103 also sits above balloon 104. The elevated position of the drainage port prevents any urine below the height of the drainage port from draining out of the bladder, resulting in the collection of residual urine. Stagnant residual urine allows for bacterial growth that may lead to infection and the aggregation of encrustations on catheter apparatus, further blocking the flow of urine.

Figure 2:
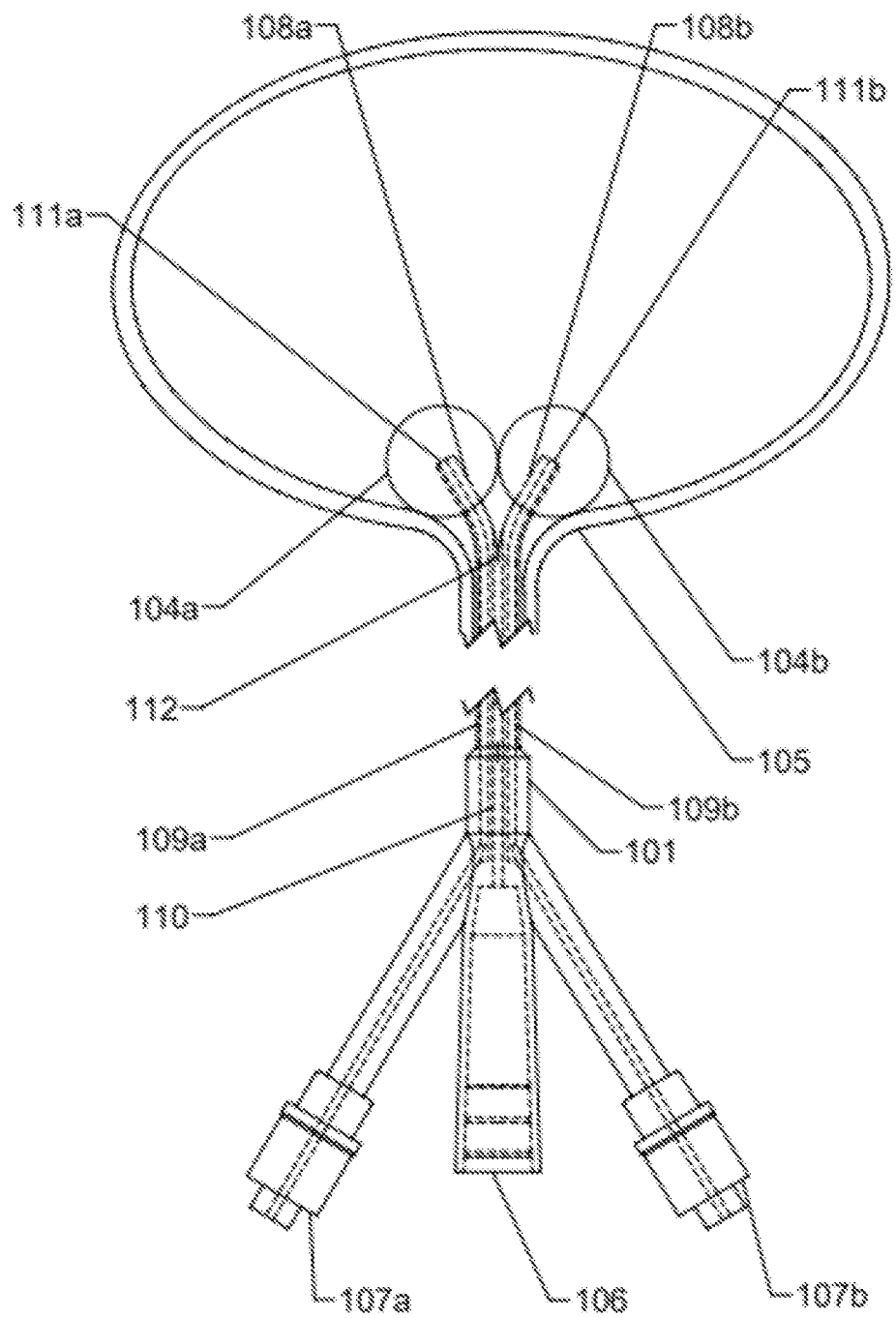
FIG. 2 illustrates a two catheter tip, two balloon configuration of the present invention in-situ.

FIG. 2 depicts a two catheter tip, two balloon configuration of the present invention, consisting of catheter tips 108a and 108b, connected to inflatable balloons 104a and 104b, respectively. Sterile water used to inflate the balloon elements can be injected from valves 107a and 107b and through valve lumens 109a and 109b, respectively. While two valves are used for better illustration, valve 107a and 107b can also be combined into one valve to inject sterile water to both valve lumens 109a and 109b simultaneously. Injected sterile water will enter each balloon through inflation ports 111a and 111b. The balloon elements function as retention elements when inflated, securing the distal end of catheter 101 within the bladder at the junction between the bladder and the urethra. Furthermore, balloons 104a and 104b also function to reveal horizontal aperture 112, with a cross section perpendicular to the flow of urine, allowing for urine to flow from bladder 105 down central lumen 110 to funnel 106 before entering an external collection bag.

Unlike concurrently used catheter designs, this invention does not use an elevated, vertical drainage port. Instead, this invention utilizes a horizontal aperture that is revealed when balloon elements expand against each other when inflated.

This horizontal aperture sits at the junction between the bladder and urethra as depicted.

The lowered position of the horizontal aperture and its horizontal orientation allows for consistent urine flow regardless of urine levels, preventing residual urine from collecting within the bladder. Balloon elements, when inflated, prevent the exposure of catheter tips, function as retention elements, and expose the horizontal aperture and the central lumen for urine drainage. The disclosed urinary catheter simulates a natural urethra, mimicking native functionality.

Figure 3A:
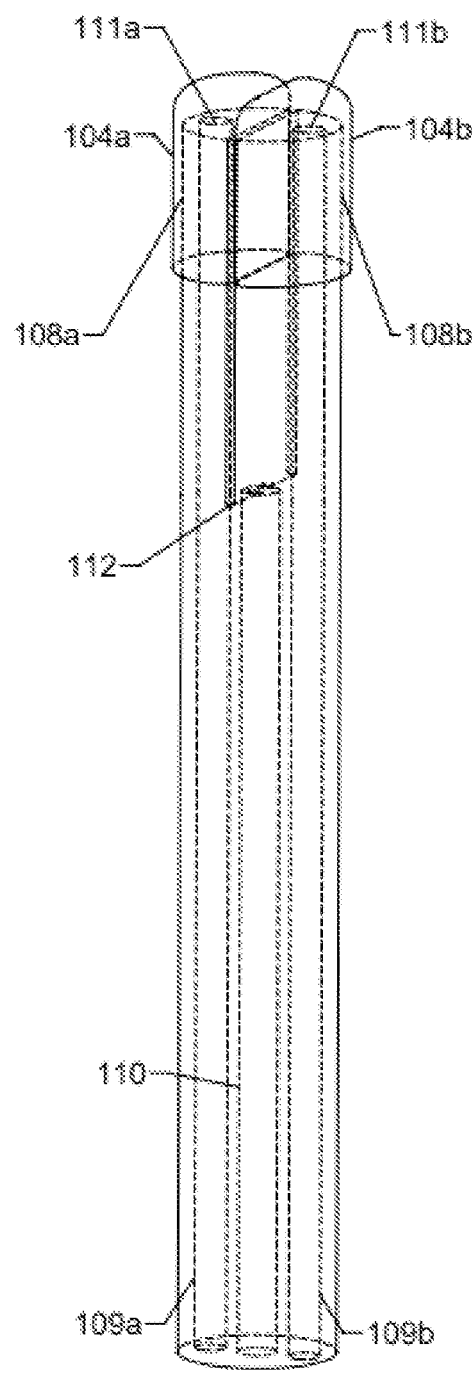
FIG. 3A illustrates a two catheter tip, two balloon configuration of present invention with deflated balloon elements by use of inflation ports located at the distal end of the valve lumen.

FIG. 3A illustrates a two catheter tip, two balloon configuration of present invention prior to inflation of balloon elements. The distal end of the catheter is divided into catheter tips 108a and 108b, enclosed by balloon elements 104a and 104b, respectively. Injected sterile water travels up valve lumens 109a and 109b to inflate balloon elements through inflation ports 111a and 111b located respectively at the distal end of the valve lumens. When balloon elements are inflated, urine drains from the horizontal aperture 112, located at the distal end of central lumen 110. However, prior to balloon inflation, horizontal aperture 112 presents as a gap between the divided tips. The conjoined tips, prior to separation by balloon elements, allow for the insertion of the catheter into the urethra and bladder.

Figure 3B:
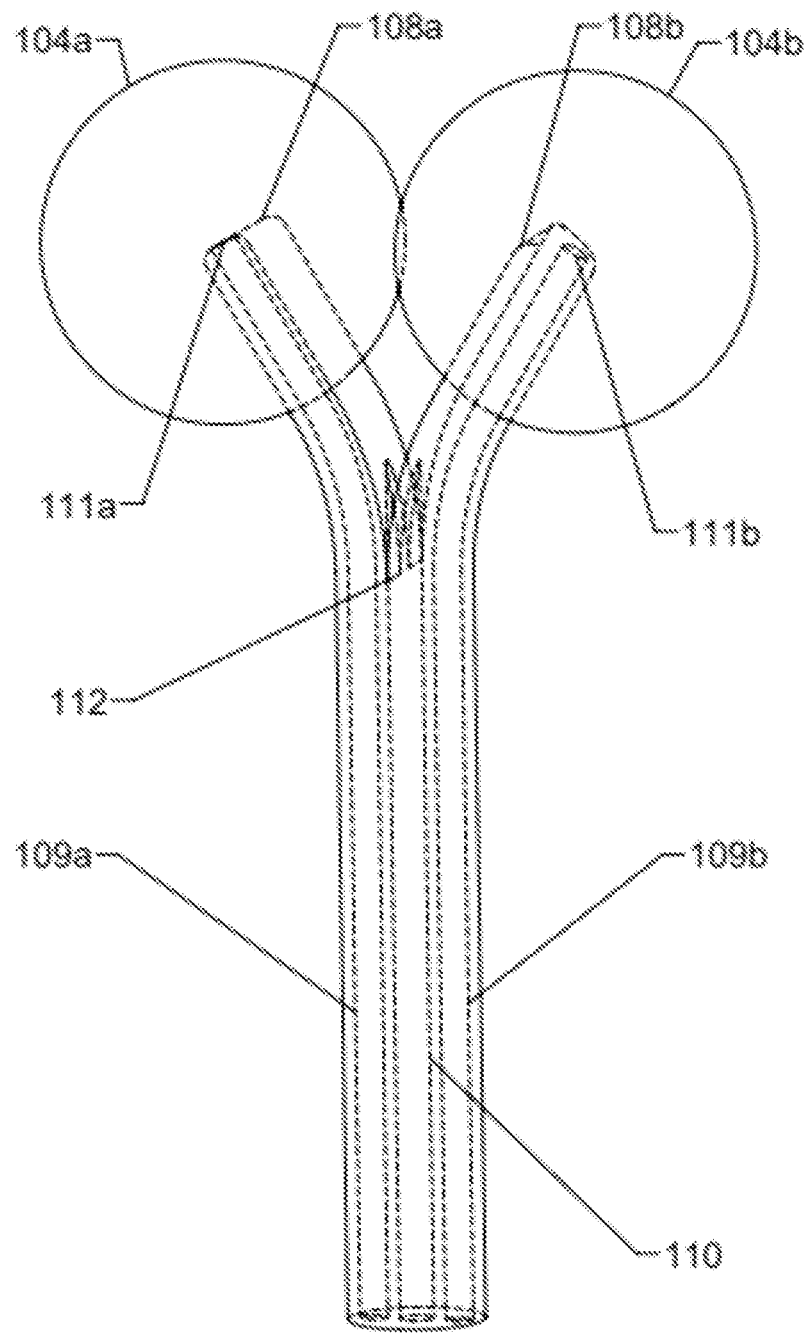
FIG. 3B illustrates a two catheter tip, two balloon configuration of present invention with inflated balloon elements by use of inflation ports located at the distal end of the valve lumens.

FIG. 3B illustrates a two catheter tip, two balloon configuration of the present invention after the inflation of balloon elements. Sterile water travels from valve lumens 109a and 109b to enter balloon elements through inflation ports 111a and 111b located respectively at the distal end of the valve lumens. Balloons 104a and 104b are configured to distend into spherical geometry, securing the distal end of the catheter within the bladder. When inflated, the balloon elements expand against each other, separating catheter tips 108a and 108b, expose horizontal aperture 112 at the distal end of central lumen 110. Unlike concurrently used catheter designs, the horizontal aperture sits at the junction of the bladder and the urethra, allowing for complete drainage of urine and prevents the collection of residual urine. Furthermore, because the horizontal aperture of this invention presents as a gap between divided catheter tips, it is characteristically dynamic and remains open during instances of body movement and changes in orientation.

Figure 4A:
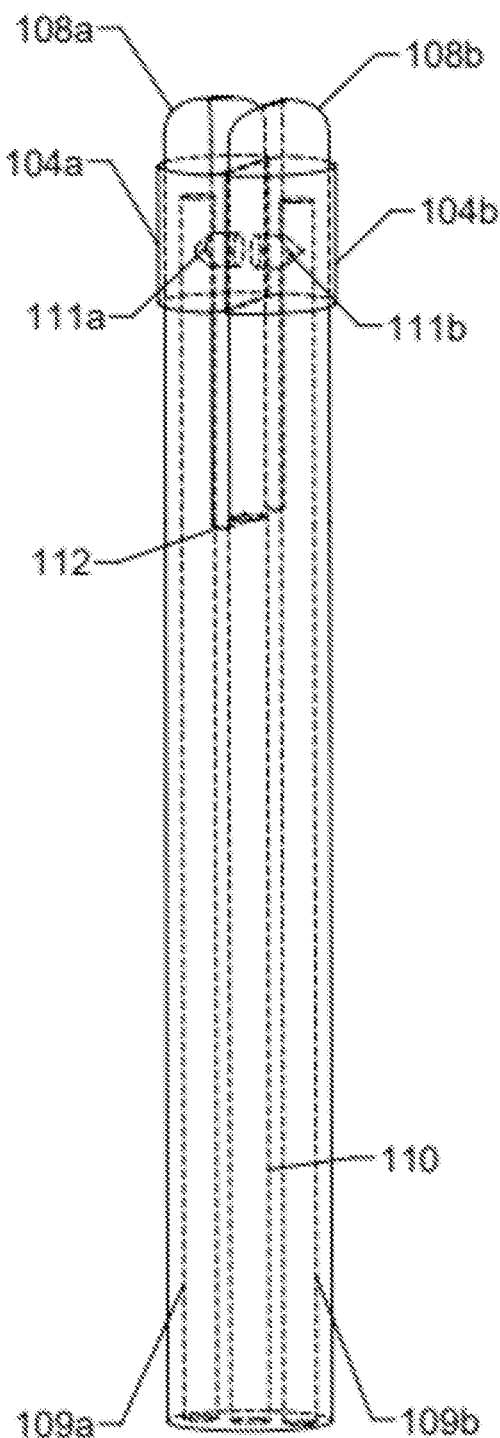
FIG. 4A illustrates a two catheter tip, two balloon configuration of present invention with deflated balloon elements connected to catheter tips using lateral inflation ports that are perpendicular to valve lumens.

FIG. 4A illustrates a two catheter tip, two balloon configuration of present invention with two deflated balloons connected to its respective valve lumens using inflation ports that lie perpendicular to the lumens. Rather than using inflation ports at the distal end of valve lumens 109a and 109b to inflate balloon elements, inflation ports 111a and 111b are located on the side of valve lumens to allow for a passageway for sterile water to flow into balloon elements. At the distal end of central lumen 110, horizontal aperture 112 presents as the gap between the two divided catheter tips.

Figure 4B:
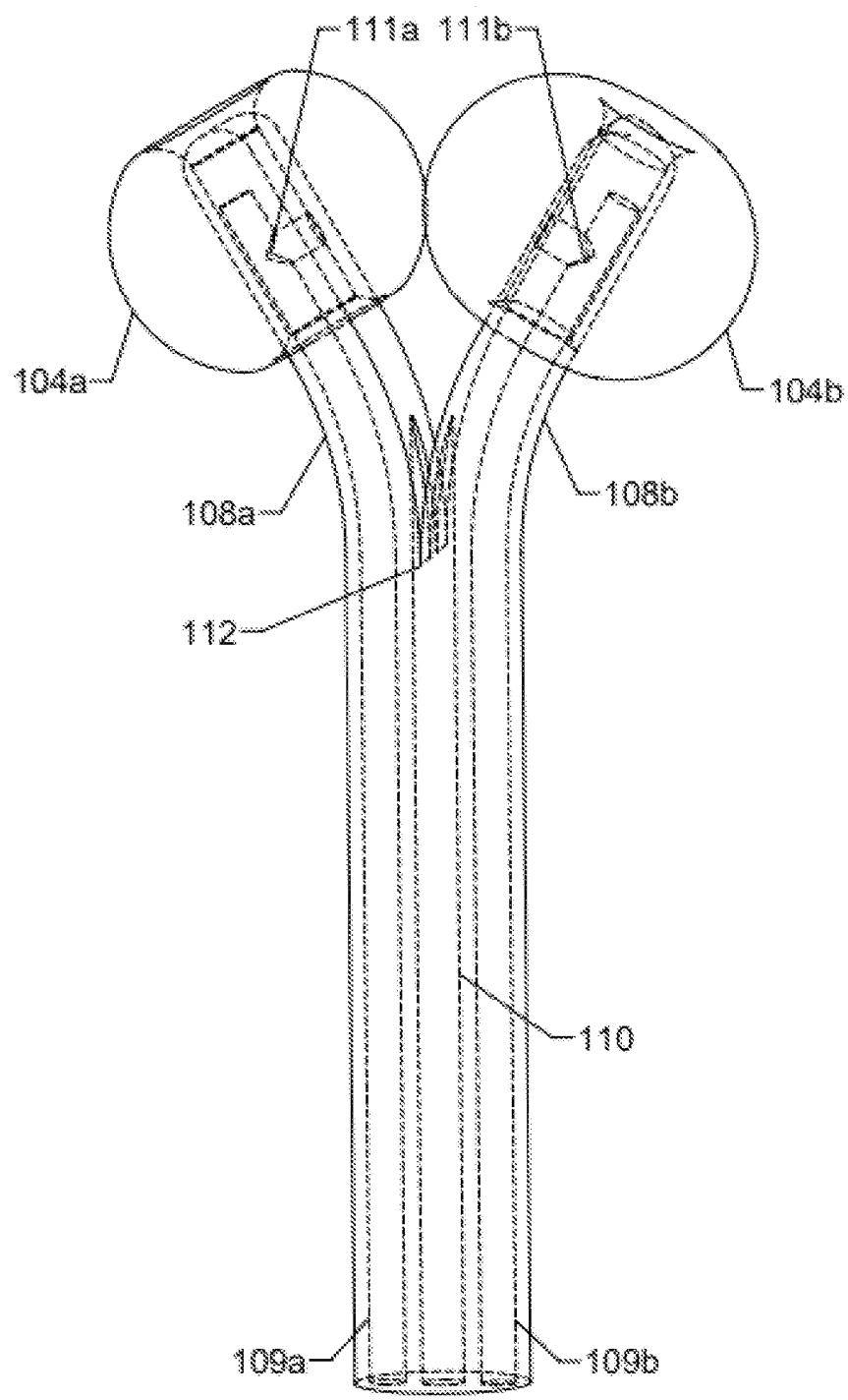
FIG. 4B illustrates a two catheter tip, two balloon configuration of present invention with inflated balloon elements connected to catheter tips using lateral inflation ports that are perpendicular to valve lumens.

FIG. 4B demonstrates a two catheter tip, two balloon configuration with two inflated balloon elements connected to its respective valve lumens using inflation ports that lie perpendicular to the lumens. Balloon elements 104a and 104b are configured and attached to encapsulate the tips once inflated. Sterile water are delivered to balloon elements by traveling up valve lumens 109a and 109b and into balloon elements through inflation ports 111a and 111b, respectively. Balloons 104a and 104b function as retention elements, but also function to expose horizontal aperture 112 when expanded against each other upon inflation. Urine drains from the horizontal aperture down central lumen 110 to and external collection bag.

Figure 5:
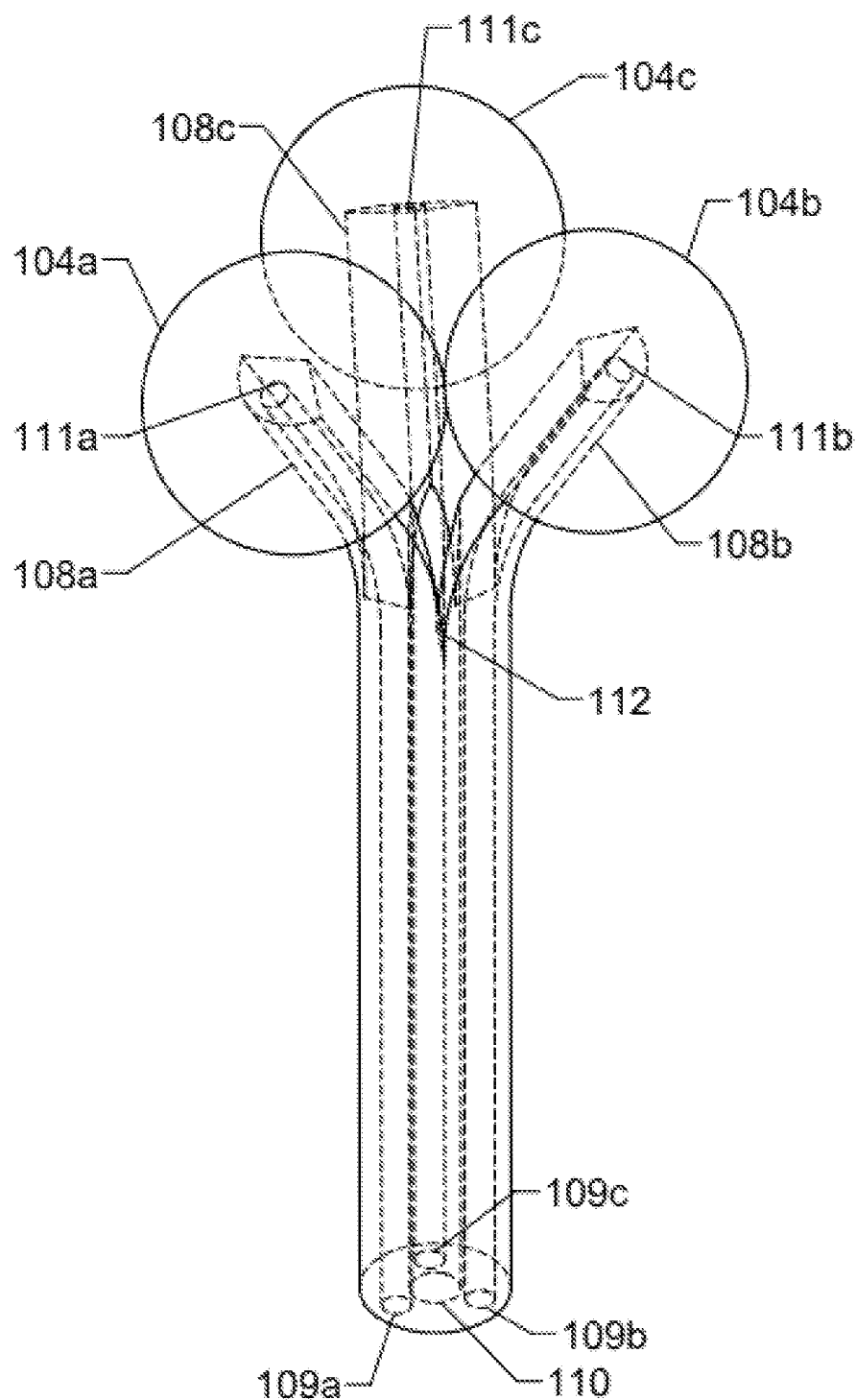
FIG. 5 illustrates a three catheter tip, three balloon configuration of present invention with inflated balloon elements.

FIG. 5 illustrates a three catheter tip, three balloon configuration of present invention with three inflated balloon elements. Balloons 104a, 104b and 104c are inflated to expand the horizontal aperture 112 located at the distal end of the central lumen 110, allowing for urine drainage down the central lumen. Balloon elements are connected to its respective catheter tip by the attachment method illustrated in either FIG. 3A or FIG. 4A.

Figure 6:
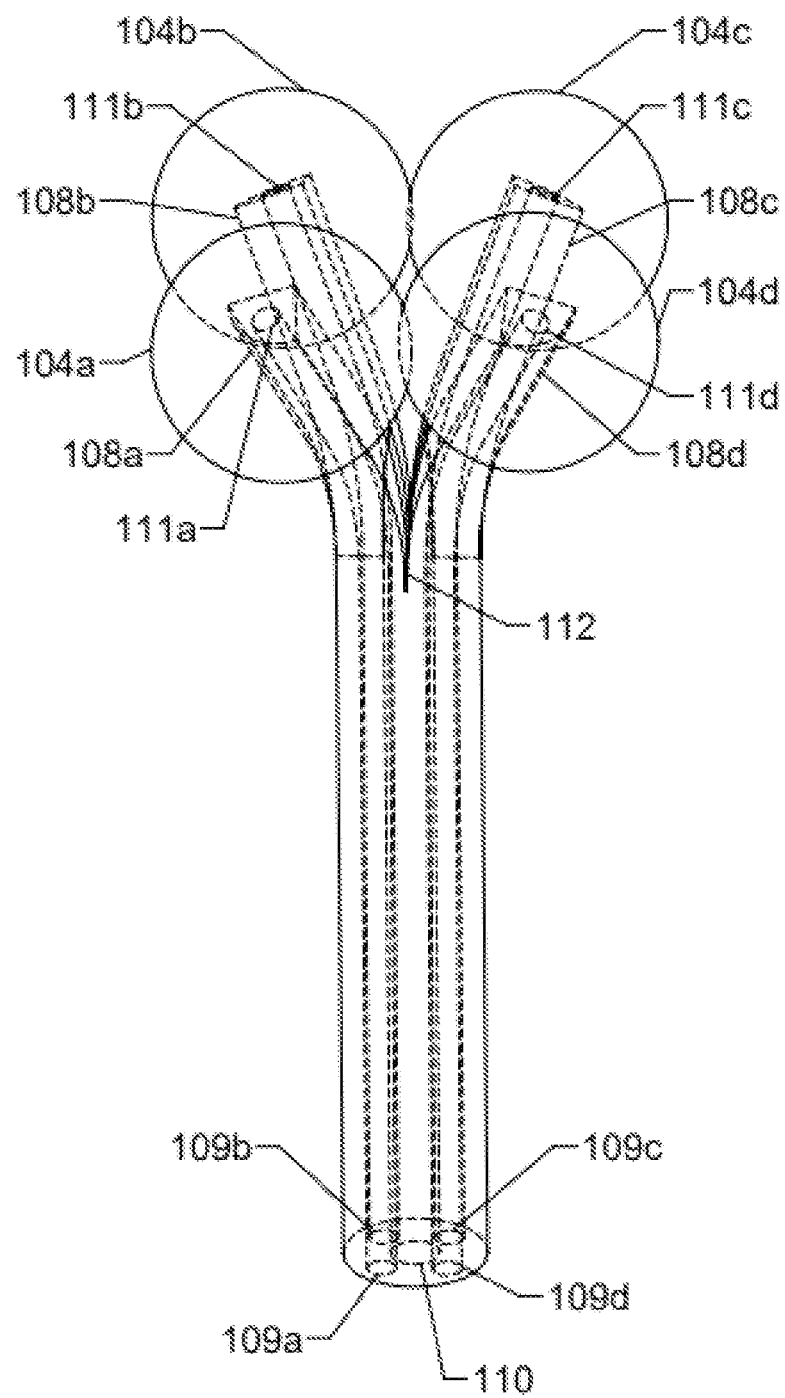
FIG. 6 illustrates a four catheter tip, four balloon configuration of present invention with inflated balloon elements.

FIG. 6 shows a four catheter tip, four balloon configuration of the present invention with four inflated balloon elements. Balloons 104a, 104b, 104c and 104d, connected to catheter tips 108a, 108b, 108c and 108d, respectively, are inflated by sterile water to expand and reveal the horizontal aperture 112 located at the distal end of the central lumen 110. Balloon elements are connected to its respective catheter tip by the attachment method in either FIG. 3A or FIG. 4A.

Figure 7:
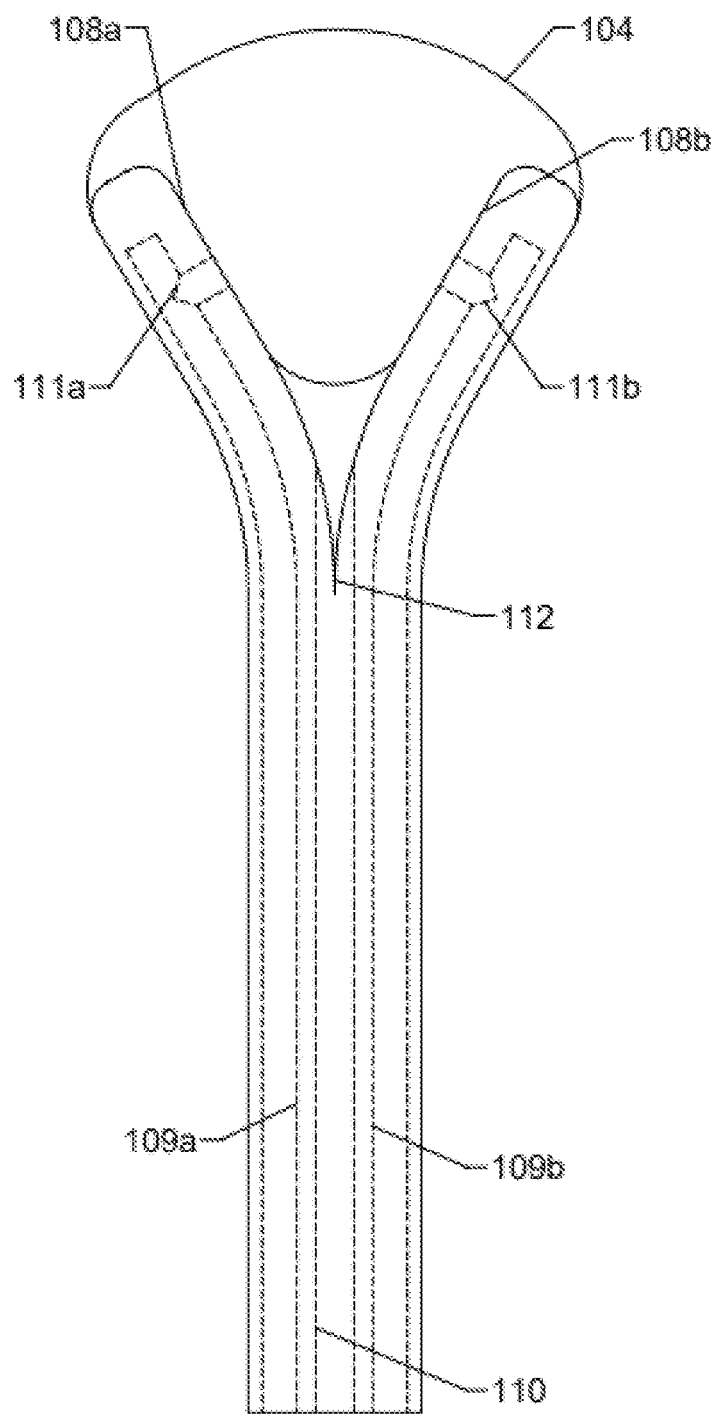
FIG. 7 illustrates a two catheter tip, one balloon configuration of present invention with an inflated balloon element.

FIG. 7 illustrates a two catheter tip, one balloon configuration of present invention with one inflated balloon element. Central balloon element 104 is expanded in between catheter tips 108a and 108b as sterile water traveling from valve lumens 109a and 109b inflates the balloon element. The balloon 104 is attached to the outer surface of catheter tips 108a and 108b. Balloon 104 is connected to catheter tips 108a and 108b through inflation ports 111a and 111b, respectively. While a perpendicular configuration is illustrated, the inflation ports can be perpendicular to the valve lumens and located on the side of each valve lumen or be positioned at the distal end of the catheter tips. Inflation of the central balloon element exposes horizontal aperture 112 located at the distal end of central lumen 110, allowing for the drainage of urine. While two valve lumens and two inflation ports are illustrated, a one balloon design can be configured so that one valve lumen and one inflation port interconnects the balloon elements with the valve.

The present invention is described in terms of detailed illustrative embodiments thereof. However, it should be understood that changes to the illustrative embodiments described above may be made without departing from the scope and intent of this present invention as described herein the claims. The drawings are not drawn to scale and are not intended to limit the full scope of the present invention.

Each illustration of the present design does not limit the quantity of balloon elements or catheter tips as this invention describes a design with two or more catheter tips and one or more balloon elements.

What is claimed is:

1. A catheter used for body urine removal comprising:
    a flexible shaft having multiple longitudinal parallel lumens with each lumen having a fixed cross-sectional dimension;
    a distal and free end divided into at least two divided tips each having a free end, said free end of said divided tips separable into a spaced condition from each other;
    a horizontal aperture formed by the separation of said free ends of said divided tips in the spaced condition from each other, said horizontal aperture located at a point of separation of said divided tips with said horizontal aperture having a cross section perpendicular to the flow of urine;
    at least two balloon elements with each of said balloon element attached to and encompassing said free end of each divided tip; and
    inflation ports located at a distal end of each of the longitudinal parallel lumens or on a side of the longitudinal parallel lumens with said balloon also encompassing said corresponding inflation port.

2. The catheter as set forth in claim 1, wherein the multiple longitudinal parallel lumens include at least one bladder urine draining central lumen and at least one balloon element inflating valve lumen.

3. The catheter as set forth in claim 2, wherein said horizontal aperture is revealed upon inflation of said balloon elements and is located at the distal end of the central lumen to allow for urine to drain from the bladder to the central lumen.

4. The catheter as set forth in claim 1, wherein said horizontal aperture comprises a gap between said divided tips before said balloon elements are inflated.

5. The catheter as set forth in claim 1, wherein each balloon of said at least two balloon elements is simultaneously inflated by use of a singular valve that connects to a respective valve lumen of each balloon or multiple valves that individually connect to the respective valve lumen of each balloon.

6. The catheter as set forth in claim 1, wherein said inflation ports create a channel between the balloon element and a valve lumen.

7. The catheter as set forth in claim 1, wherein said inflation ports are located at a distal end of a valve lumen or arranged perpendicular to and on a side of each valve lumen.

8. The catheter as set forth in claim 1, wherein said balloon elements are inflated through valve lumens and the inflation ports.

9. A catheter used for body urine removal comprising:
- a flexible shaft having multiple longitudinal parallel lumens with each lumen having a fixed cross-sectional dimension;
- a distal and free end divided into at least two divided tips each having a free end in a spaced condition from each other,
- a horizontal aperture formed by the separation of said free ends of said divided tips in the spaced condition from each other, said horizontal aperture located at a point of separation of said divided tips with said horizontal aperture having a cross section perpendicular to the flow of urine;
- at least one balloon element attached to and encompassing said free ends of said divided tips; and
- an inflation port located at the distal and free end of each of said longitudinal parallel lumens or on a side of the longitudinal parallel lumens with said balloon encompassing said inflation ports.

10. A catheter used for body urine removal comprising:
- a flexible shaft having multiple longitudinal parallel lumens with each lumen having a fixed cross-sectional dimension;
- a distal and free end divided into at least two divided tips each having a free end in a spaced condition from each other,
- a horizontal aperture formed by the separation of said free ends of said divided tips in the spaced condition from each other, said horizontal aperture located at a point of separation of said divided tips with said horizontal aperture having a cross section perpendicular to the flow of urine;
- at least one balloon element attached proximal to said free ends of each of said divided tips; and
- an inflation port located on a side of the longitudinal parallel lumens with said balloon encompassing said inflation ports.

11. The catheter as set forth in claim 10, wherein said singular balloon element is inflated through a singular valve that connects to a valve lumen of the balloon.

* * * * *